US009204997B2

(12) United States Patent
Paulson et al.

(10) Patent No.: US 9,204,997 B2
(45) Date of Patent: Dec. 8, 2015

(54) GOGGLE LENS ENGAGEMENT SYSTEM

(76) Inventors: Roy Paulson, Temecula, CA (US);
Fernando Mota, Moreno Valley, CA (US)

(*) Notice: Subject to any disclaimer, the term of this patent is extended or adjusted under 35 U.S.C. 154(b) by 742 days.

(21) Appl. No.: 12/005,682

(22) Filed: Dec. 28, 2007

(65) Prior Publication Data
US 2008/0155736 A1    Jul. 3, 2008

Related U.S. Application Data

(60) Provisional application No. 60/877,493, filed on Dec. 28, 2006.

(51) Int. Cl.
*A61F 9/02* (2006.01)
*G02C 9/04* (2006.01)

(52) U.S. Cl.
CPC .. *A61F 9/025* (2013.01); *G02C 9/04* (2013.01)

(58) Field of Classification Search
CPC .................................. A61F 9/025; G02C 9/04
USPC ...................... 2/438, 439, 448, 451
See application file for complete search history.

(56) References Cited

U.S. PATENT DOCUMENTS

| 2,677,824 | A | * | 5/1954 | Gay, Jr. et al. | 2/441 |
|---|---|---|---|---|---|
| 3,718,937 | A | * | 3/1973 | Smith | 2/436 |
| 5,410,763 | A | * | 5/1995 | Bolle | 2/436 |
| 7,343,631 | B2 | * | 3/2008 | Lin | 2/448 |
| 2005/0036103 | A1 | * | 2/2005 | Bloch | 351/116 |
| 2007/0234526 | A1 | * | 10/2007 | Chen | 24/265 R |
| 2009/0313746 | A1 | * | 12/2009 | Wang | 2/431 |

* cited by examiner

*Primary Examiner* — Katherine Moran
(74) *Attorney, Agent, or Firm* — Donn K. Harms

(57) ABSTRACT

A locking mechanism to prevent unintentional disengagement of a goggle lens from its frame and allowing for easy changes of the lens when required. The locking mechanism employs translatable clips engaged to the frame which translate toward and away from the lens between engaged and disengaged positions. The engaged position locks the lens in place until the user translates the clip to the disengaged position. A post and slot engagement of each clip to the frame maintains them connected to the frame to prevent loss.

5 Claims, 2 Drawing Sheets

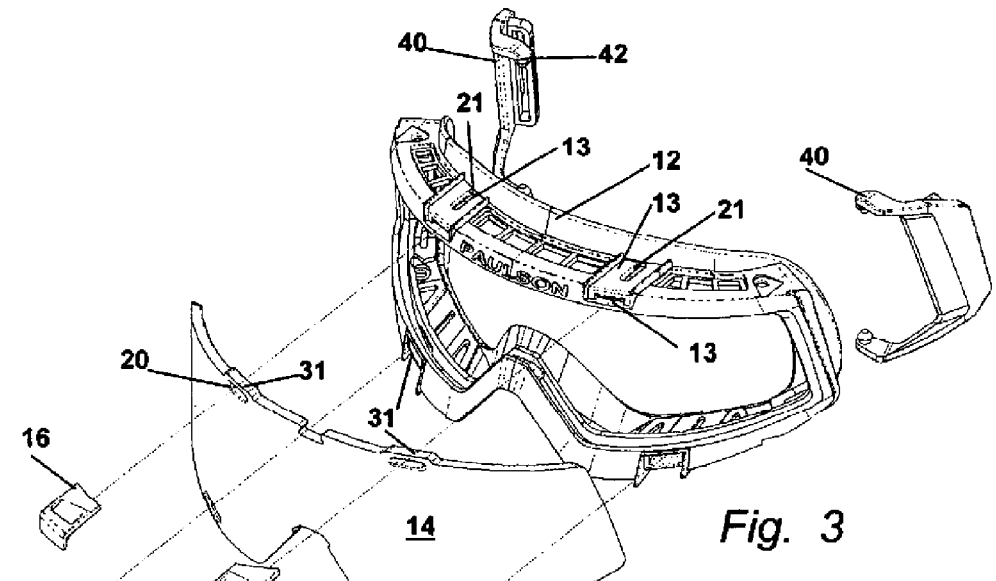
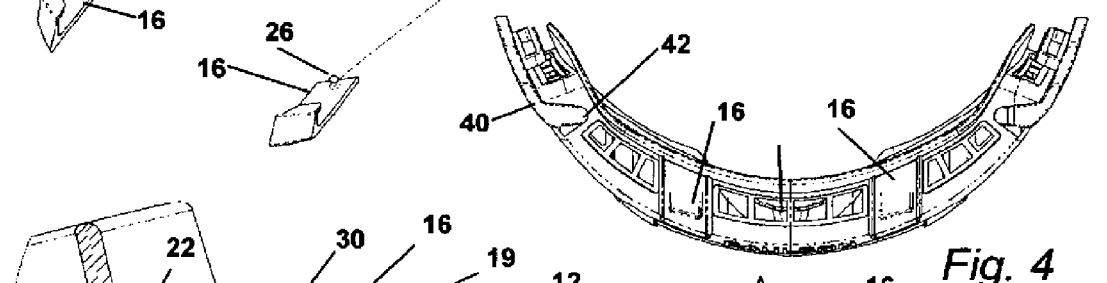
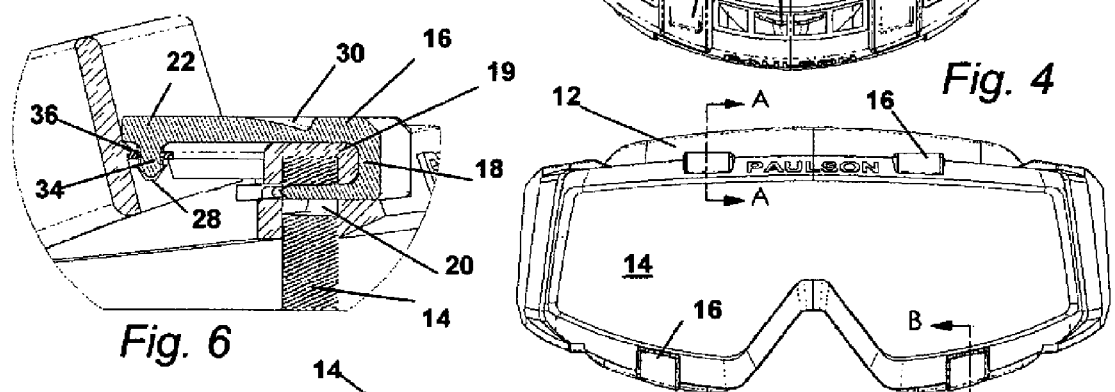
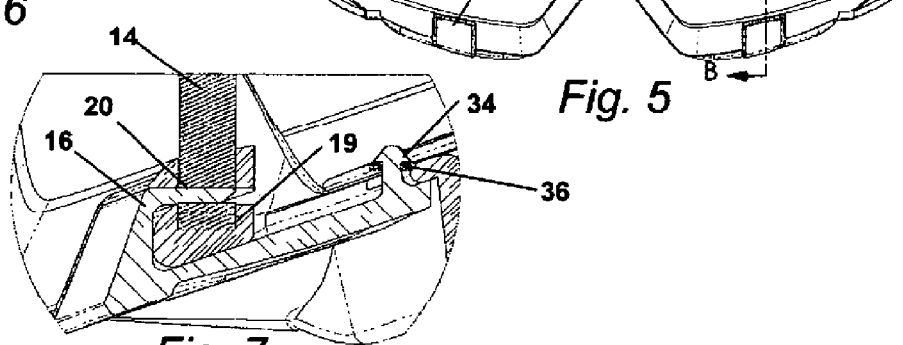
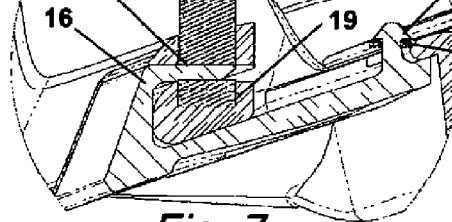

GOGGLE LENS ENGAGEMENT SYSTEM

FIELD OF THE INVENTION

This application claims the benefit of, U.S. Provisional Patent Application Ser. No. 60/877,493, filed Dec. 28, 2006 and incorporated herein in its entirety by reference.

The disclosed system and method relate generally goggles employed over the eyes. More particularly it relates to a goggle adapted for easy replacement of lenses in a sealed engagement with the goggle frame which is easy to employ without losing parts integral the operation of the device.

BACKGROUND OF THE INVENTION

Goggles have been employed to protect the eyes of users and in some cases enhance vision, for many years. When worn by a user for eye protection, goggles are especially well adapted to keep dust, wind, gravel, and other particulate out of the eyes of the user. In dry and windy environments such as with the military in a desert environment, goggles are frequently employed to prevent vision impairment that can be caused by wind drying the eyes and particulate entering the eyes. Further, in most environments, goggles may be employed with lens tinting and polarization to both enhance vision and protect the user's eyes from long term exposure to different light spectrums.

However, in many environments, it is particularly useful if the lens engaged with the goggle frame may be replaced or substituted or temporarily removed. Replacement is frequently required when the lens becomes scratched or otherwise damaged. Temporary removal or a substitution of one lens for another from a plurality of cooperatively engageable lenses is particularly useful when the environment of the user changes their vision requirements. For instance if used in a desert environment by the military, during the day a lens which reduces glare and eye damage from radiation and which enhances vision is particularly useful since a soldier depends upon their eyesight for their well being. However that same user in a nighttime employment of goggles in the same environment, may wish to have a clear lens which allows more light to their eyesight or a partially tinted lens which enhances night vision but would not be particularly useful during daylight. On some occasions a temporary removal of the lens may be desirable to allow for temporary unaltered vision.

In order to allow for removal and replacement some type of lens retainment system is required. Historically goggle lenses have been retained by various locking mechanisms that essential operate by friction. Systems have been employed using tapered openings in the frame adapted for a frictional seal around the perimeter of the lens therein. Additionally methods historically employed for lens retainment include shaped indents, hooks, and bezels that surrounded the entire frame and lens.

The basic problem attempted by such prior art is to securely engage the lens in the goggle frame but also allow for an easy change in the field. While the goal of the retainment-system is easy use, the lens must still be secured to resist disengagement in case of impact upon the lens, or distortion of the conventionally flexible goggle frame by brute force.

In most such prior systems, distortion of the frame if the lens is not mechanically engaged to the frame by other than engagement in a slot, will cause the lens to pop out of the frame. The same disengagement with a frictional seal type lens and goggle will occur upon a sharp impact to the semi-rigid lens.

However, if a mechanical engagement of the lens to the frame is employed, other problems occur in that they can be hard to engage and disengage by the user or hard to employ when the user is wearing gloves. Further, if pins and clips are used to mechanically engage the lens to the frame, once separated from the frame, they tend to become lost rendering the goggle useless.

Accordingly, there is an unmet need for a goggle having a very secure engagement means for the lens to the goggle frame which provides a mechanical mechanism to hold the lens in a secure engagement. While providing a positive lock of the lens to the frame, such a device must also be easy to operate. Such a goggle engagement system should require no tools to operate since goggles are frequently employed in harsh conditions or in military situations not conducive to tool employment. Further, such a device must insure that all parts employed to lock the lens to the goggle frame, resist becoming lost during a lens disengagement.

In this respect, before explaining at least one embodiment of the invention in detail it is to be understood that the invention is not limited in its application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for designing other mechanical engagement systems for lenses to goggles and for carrying out the several purposes of the present invention. It is important, therefore, that the claims be regarded as including such equivalent construction insofar as they do not depart from the spirit and scope of the present invention.

An object of this invention is the provision of a goggle having a lens which is engaged to the goggle frame by a mechanical lock to thereby resist disengagement of the lens from impacts or from contortions of the flexible goggle frame.

A further object of this invention is to provide such a goggle with a lens retainment system which is easy to operate and requires no tools to engage or disengage a lens with the frame.

An additional object of this invention is the provision of such a goggle and lens retainment system which prevents the loss of lens engagement parts during use or lens replacement.

These together with other objects and advantages which will become subsequently apparent reside in the details of the construction and operation as more fully hereinafter described and claimed, reference being had to the accompanying drawings forming a part thereof, wherein like numerals refer to like parts throughout.

SUMMARY OF THE INVENTION

The disclosed system provides a means for easy interchangeability of lenses in a goggle which overcoming the noted shortcomings of lens dismount and lost parts of the prior art. The device employs a goggle frame and a lens which is dimensioned for a removable sealed engagement with the frame.

Engagement of the lens and frame are insured against an accidental dismount from impacts and contortions of the frame by the employment of a plurality of clips which are slidably engaged to the frame in ramps and translate between an engaged position locking both the lense and clip in position, to a disengaged position where the clip is still in an engagement with the frame to thereby avoid lost parts. A U-shaped first end of the clip is employed to communicate through an aperture in the lens to mechanically hold it in place and a sealed engagement around its periphery.

A second end of the clips are each adapted for retained engagement with the frame during translation and dismount of the lens. In operation, when translated to the disengaged position of the clip, the first end of the clip will disengage from the lens aperture allowing its removal from the frame.

A means for locked engagement of the lens to the frame and clip in the engaged position is provided by a locking mechanism of the clip and frame. Means to maintain the clip engaged to the frame is provided by a recess formed in the ramp in which the clip translates using a member projecting from the second end of the clip engaged in a slot in the ramp. Once in the engaged position the member locks into an elastic locking aperture and must be forcibly pulled therefrom with sufficient force to overcome the grip of the locking aperture on the member protruding from the clip.

The low profile design of the clip and translation within a ramp formed into the surface of the frame is also especially preferred. This recessed translational engagement maintains the exposed surface of the clip from interfering with a helmet worn by the user. Helmet wear is also aided by provision of rotationally engaged strap mounts which allow for engagement at a wide variety of angles.

In this respect, before explaining at least one embodiment of the device and method herein in detail, it is to be understood that the invention is not limited in its application to the details of construction, and to the arrangement of the components or method steps set forth in the description herein. The invention is thus capable of other embodiments and of being practiced and carried out in various ways as would occur to those skilled in the art once they have read this disclosure.

As such, those skilled in the art will appreciate that the conception upon which the disclosed goggle with removably engageable lens in a positive lock is based may readily be utilized as a basis for the designing of other methods for carrying out the purposes of the present invention. It is important, therefore, that the claims be regarded as including such equivalent construction insofar as they do not depart from the spirit and scope of the present invention.

Also with respect to the disclosure herein, it is to be realized that the optimum relationships for the method and hardware herein are to include variations in function and manner of operation, steps in operation and use, which are readily apparent and obvious to one skilled in the art, and all equivalent relationships to those illustrated in the drawings and described in the specification are intended to be encompassed by the present invention. Therefore, the disclosure herein is considered as illustrative only of the key principles of the invention yielding the improved operation thereof. Further, since numerous modifications and changes will readily occur to those skilled in the art, it is not desired to limit the invention to the exact construction and operation shown and described, and accordingly, all suitable modifications and equivalents which may be resorted to by those skilled in the art are considered to fall within the scope of the invention.

BRIEF DESCRIPTION OF DRAWINGS

FIG. 3 depicts an exploded perspective view of the disclosed device.

FIG. 4 depicts a top view of the goggle showing engagement clips engaged with the frame and mechanically locking the lens in a sealed engagement.

FIG. 5 depicts a front view of the device of FIG. 4.

FIG. 6 is a slice through FIG. 5 along line A-A.

FIG. 7 is a slice view through FIG. 5 along line B-B.

DETAILED DESCRIPTION OF PREFERRED EMBODIMENTS

Figure 1:
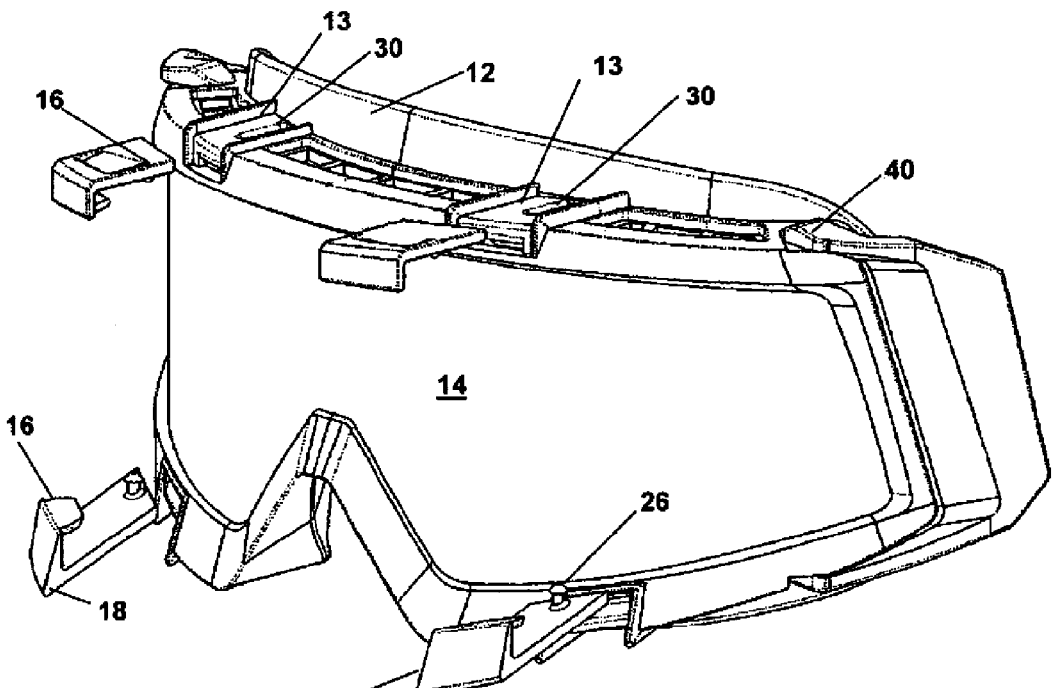
FIG. 1 is a graphic depiction of a front perspective view of the goggle herein showing engagement clips aligned with slots in the lens and goggle.

Referring now to the drawings in FIGS. 1-8 singularly or in combination, wherein similar parts are identified by like reference numerals, some preferred embodiments of the device 10 disclosed herein in current preferred modes are shown and described.

Figure 8:
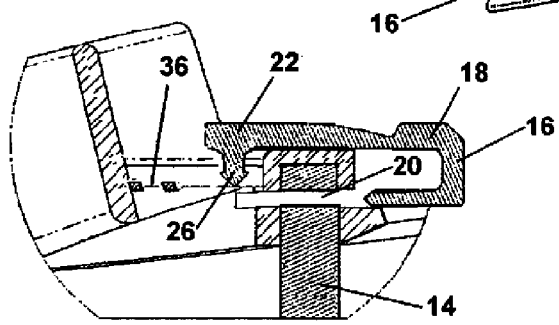
FIG. 8 depicts the clip translated to a disengaged position from the engaged position of FIG. 6.
Figure 2:
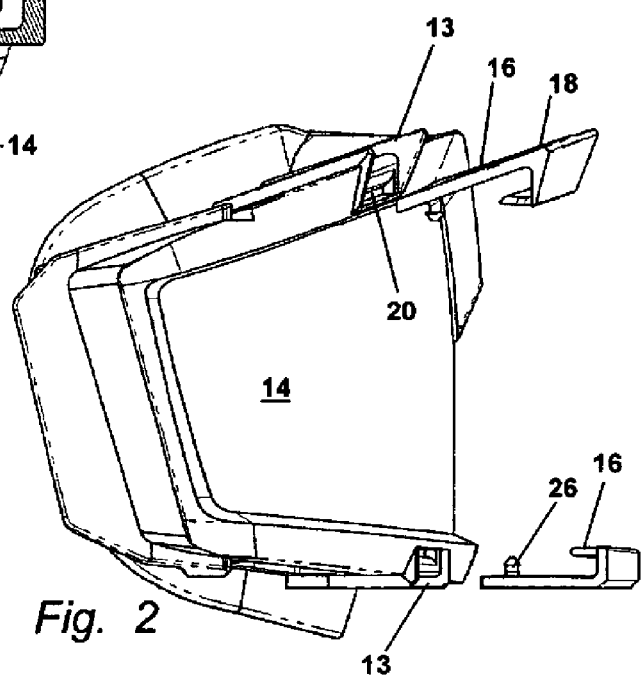
FIG. 2 depicts a side view of the goggle of FIG. 1.

As seen in the front perspective view of FIG. 1 the device employs a goggle frame 12 and lens 14 which is adapted for a removable sealed engagement with the frame 12 and to be held securely using a plurality of clips 16 which are slidably engaged to the frame 12 in ramps 13 to provide translation between an engaged position shown in FIG. 6 to a disengaged position of FIG. 8. Each clip 16 has a first end 18 adapted for engagement with the exterior surface of the lens 14 once the clip 16 is translated to and engaged position with the frame 12 as shown in FIGS. 5-6 from the disengaged position of FIG. 8. Currently the preferred mode of engagement of the first end 18 of the clip 16 to the lens 14 employs an engagement of the portion of the first end 18 through an aperture 20 communicating through the lens 14 which is located adjacent to the periphery edge of the lens 14.

The clips 16 have a second end 22 which is adapted for retained engagement with the frame 12. The clip 12 employs a novel means to maintain engagement with the frame 12 while in the disengaged position and thereby maintains the clips 16 connected to the frame 12 while the lens 14 is disengaged or being replaced with another lens 14 and prevents the clip 16 from becoming lost. This is a most important feature as noted since the device 10 is employed for use in some very unfavorable conditions. In operation, when translated to the disengaged position of FIG. 8, the first end 18 of the clip 16 disengages from the aperture 20 in the lens 14 allowing its removal from the frame 12. Sliding the clip 16 is accomplished by the user's finger imparting a lateral force on the top side of the clip 16 in a depression 17 to slide it in the ramp 13. While a frictional engagement with the top of the clip may work, providing the depression 17 allows the user to impart more lateral force in the direction of the slide of the clip 16 intended.

Substitution of another lens 14 from a plurality of lenses available or replacement of the lens 14 with another lens 14 is in reverse of removal. The lens 14 is placed in a sealed engagement with the frame 12 which in the current preferred mode is engaging the tab 31 of the lens 14 into a recess 19 formed into the frame 12. The recess 19 provides means for sealed engagement of the lens 14 with the frame 12 to form an interior chamber between the face of a user and the lens 14 and the frame 12 engaged on the face.

As noted, the sealed engagement of the lens 14 is subject to unwanted disengagement from impact and deformation. When mounting the lens 14 with the frame 12, a means for locked engagement of the lens 14 to the frame 12 is provided by translating the clip 16 to the engaged position of FIG. 6 with the first end 18 communicating through the aperture 20 of the lens 14. Means to maintain the clip 16 engaged to the frame 12 when disengaged is provided by a recess 30 formed in the ramp 13. The recess 30 has flexible top covering sidewalls overhanging the recess 30 with a gap 21 therebetween and maintains the clip 16 engaged to the frame 12 using a member 26 projecting from the second end 22. The member 26 has a distal end 28 which is preferably tapered toward a ridge 34 projecting from the exterior circumference 35 of the lower portion of the member 26. The ridge 34 is slightly larger than the gap 21 between the flexible overhanging sidewalls at the top of the recess 30 such that once it stretches the sidewalls to project the distal end 28 into the recess 30 past the ridge 34, subsequently the member 26 is not easily removed but will still slide in the recess 30 to allow translation between the engaged and disengaged positions.

In operation as the clip 16 is slid toward the user forehead or second end 22 by the finger of the user, to translate the clip 16 to the engaged position, the second end 22 of the clip will flex slightly and allow the distal end 28 of the member 26 on the clip 16 to project through a locking aperture 36 depending into the bottom surface of the recess 30. The diameter of the locking aperture 36 is elastic in nature such that it will stretch to allow the tapered end of the member 26 to stretch over it and allow the larger ridge 34 to engage through the locking aperture 36. This engagement of the ridge 34 with the locking aperture 36 is maintained until sufficient lateral force is imparted on the clip 16 to slide it to the disengaged position and to concurrently pull on the member 26 to stretch the locking aperture 36 over the projecting ridge 34 to thereby release the distal end of the member 26 to allow it to translate toward the first end 18. Absent sufficient lateral force to release the member 26 from the locking aperture 36, the clip 16 will remain locked in the engaged position with the first end 18 engaged through the aperture 20 in the lens 14 locking it in place also.

Thus engagement of the distal end of the member 26 with the locking aperture 36 provides means to lock the clip 16 in the engaged position to maintain the lens 14 locked in the frame 12. Engagement of the distal end of the member 16 within the recess 30 provides means to maintain the clip 16 in engagement with the frame 12 when translated to the disengaged position to allow lens 14 removal and/or replacement.

Thus, the locking clip 16 provides a manner to overcome the noted easy disengagement of the lens 14 from the frame 12 on impact or distortion of the flexible frame 12 suffered by conventional goggles. The engagement of the clip 12 in the recess 30 during translation back and forth, provides a manner to keep the clip 16 from becoming lost when the lens 14 is disengaged. Both functions as noted are extremely important in the hostile environment where goggles are employed and lost or accidentally disengaged parts can render the device useless.

The low profile design of the clip 16 and translation within a ramp 13 in the surface of the frame 12, is also especially preferred in the device 10. In a military or motorcycle use, or other uses where a helmet is worn, the clip 16 and resulting locking system and the means to maintain engagement of the clip with the frame 12, in a low-profile provided by the recessed ramp engagement. This recessed translational engagement maintains the exposed surface of the clip 16 from projecting too far above the upper exterior surface of the goggle frame 12 where it might impede the wearing of a helmet by interfering with the front edge of the helmet were it to project above the top surface.

The device 10 herein can thus be practiced by forming or placing the lens locking and maintaining components on a conventional goggle frame already in existence or can be formed as a complete unit with the lens locking components formed into the goggle frame 12 as noted above. If employed as a lens locking system on a conventional goggle, the recess 30 with the overhanging top wall can be formed in the top surface of the goggle body 12 and sized to engage the ridge 34 at the distal end of a clip 16. This engagement as with the combined device 10 above, provides means to maintain the clips 16 in contact with the frame 12 and not become lost. Provision of the locking aperture 36 at the rear of the recess 30 will likewise provide means to maintain the clips 16 locked in the engaged position allowing the first ends 18 of the clips 16 to hold the lens 14 in its sealed engagement with the frame 12.

Additionally, since the lenses 14 of the device 10 have the apertures 20 formed to align with the ramps 13 formed on the frame 12, and have registration tabs 31 located on the periphery that line up with frontal portions of the ramps 13, it is especially easy, even in a dark or otherwise vision-impaired environment, to change the lens 14. The tabs 31 are positioned to extend from the edge of the lens 14 and engage respective ramps 13 and thereby align the lens 14 for clip engagement. Thus, any lens 14 from a supply or kit of lenses 14 having the same tabs 31 and apertures 20 positioned for such alignment with the ramps 13 will easily drop into place even using the fingers in a no-light situation since the user can feel the tab and ramp engagement.

Once so aligned, the user thus will impart lateral force on the clip 16 to engage them through the apertures 20 and subsequently lock the clips 16 and lens 14 in a registered sealed engagement with the frame 12.

Finally, to aid in maintaining a good seal with the face of the user and to adapt to the various facial structures of different people, and to allow storage of the device 10 by engaging it on a helmet, the device 10 is equipped with pair of strap mounts 40 that are rotatably engaged at a hinge point 42 on the frame 12. This rotational or hinged engagement of the strap mounts 40 allows the elastic strap that engaged therebetween to angle outward from the frame or inward as required by the shape of the user's head or the helmet on which it is mounted.

As noted previously, the disclosed goggle having a locking engagement for lenses shown in the drawings and described in detail herein, disclosed arrangements of elements of particular construction, and configuration for illustrating preferred embodiments of structure and method of operation of the present invention. It is to be understood, however, that elements of different construction and configuration and different steps and process procedures and other arrangements thereof, other than those illustrated and described, may be employed for providing the method herein within the spirit of this invention.

As such, while the present invention has been described herein with reference to particular embodiments thereof, a latitude of modifications, various changes and substitutions are intended in the foregoing disclosure, and it will be appreciated that in some instance some features of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

What is claimed is:

1. In a goggle, having a flexible frame and a lens carried by said frame, and improvement in the form of a locking mechanism to prevent unintentional disengagement of said lens from said frame, said locking mechanism comprising:

at least one clip translatabley engaged with said frame;

said clip translatable between a first position disengaged from said lens to a second position forming a locked engagement between said lens and said frame,
said clip having a first end and a second end;
a member extending from said second end of said clip;
said member communicating through an engagement aperture formed in said frame when said clip is translated to said second position;
said engagement aperture dimensioned to form a frictional engagement with said member;
a ridge projecting from said member;
said ridge forming a portion of said member to a size larger than a diameter of said engagement aperture;
at least one aperture communicating through said lens;
a component extending from said first end of said clip; and
said component engaging through said aperture when said clip is translated to said second position; and
translation of said clip to said first position requiring a force sufficient to stretch said engagement aperture over said ridge.

2. The improvement to the goggle of claim 1 additionally comprising:
a plurality of said apertures communicating through said lens;
a plurality of said clips each having a respective said component extending from a first end of said clip; and
each respective said component engaging through a respective said aperture when each said clip is translated to said second position.

3. The improvement to the goggle of claim 2 additionally comprising:
said component extending from a respective said first end of each of said clips being a substantially U-shaped portion of said respective first end of each of said clips.

4. The improvement to the goggle of claim 1 additionally comprising:
said component extending from said first end of said clip being a substantially U-shaped portion of said first end of said clip.

5. The improvement to the goggle of claim 1 additionally comprising:
a plurality of tabs extending from a perimeter of said lens;
each of said tabs aligned for an engagement with a respective depression formed in said frame; and
said engagement providing means to register said lens in proper position for said engaging of said component through said aperture when said clip is translated to said second position.

* * * * *